(12) United States Patent
Mishima et al.

(10) Patent No.: US 6,458,114 B1
(45) Date of Patent: Oct. 1, 2002

(54) DISPOSABLE DIAPER

(75) Inventors: Yoshitaka Mishima; Toshifumi Otsubo, both of Kagawa-ken (JP)

(73) Assignee: Uni-Charm Corporation, Ehime-ken (JP)

( * ) Notice: Subject to any disclaimer, the term of this patent is extended or adjusted under 35 U.S.C. 154(b) by 26 days.

(21) Appl. No.: 09/654,023

(22) Filed: Sep. 1, 2000

(30) Foreign Application Priority Data

Sep. 3, 1999 (JP) .......................................... 11-249951

(51) Int. Cl.[7] .............................................. A61M 15/00
(52) U.S. Cl. ...................... 604/385.24; 604/385.101; 604/385.19; 604/385.24; 604/385.26
(58) Field of Search ................................ 604/346–348, 604/385.01, 385.14, 385.19, 385.24–385.3, 393–402

(56) References Cited

U.S. PATENT DOCUMENTS

| | | | | |
|---|---|---|---|---|
| 2,277,043 A | * | 3/1942 | Cohn | 604/348 |
| 2,944,551 A | * | 7/1960 | Breer | 604/347 |
| 5,904,674 A | | 5/1999 | Bonjour | |
| 6,168,583 B1 | * | 1/2001 | Tanji et al. | 604/385.14 |
| 6,293,937 B2 | * | 9/2001 | Matsushita | 604/385.19 |

FOREIGN PATENT DOCUMENTS

| | | |
|---|---|---|
| EP | 0 486 006 | 5/1992 |
| EP | 0 911 006 | 4/1999 |
| GB | 2 280 374 | 2/1995 |
| JP | 5-277149 | 10/1993 |
| WO | 97/17920 | 5/1997 |

OTHER PUBLICATIONS

Copy of European Search Report dated Jun. 20, 2001.

* cited by examiner

Primary Examiner—John G. Weiss
Assistant Examiner—Karin M. Reichle
(74) Attorney, Agent, or Firm—Baker & Daniels

(57) ABSTRACT

A disposable diaper having an absorbent body that includes a topsheet, a backsheet, a core disposed therebetween. A first barrier wall annularly extends above a top surface of the topsheet. The first barrier wall lies in a rear half section of the absorbent body and is fixed to the absorbent body along a lower peripheral portion thereof so as to define a first opening in a substantially central zone of the first barrier wall. A second barrier wall annularly extends around the first barrier wall over both the front and rear half sections of the absorbent body. A lower peripheral edge portion of the second barrier wall is fixed to the peripheral portion of the absorbent body so as to define a second opening in a substantially central zone of the second barrier wall.

4 Claims, 3 Drawing Sheets

DISPOSABLE DIAPER

BACKGROUND OF THE INVENTION

This invention relates to a disposable diaper for absorption and containment of excretion. Japanese Patent Application Disclosure No. 1993-277149 describes a disposable diaper comprising a liquid-pervious topsheet, a liquid-impervious backsheet, a liquid-absorbent core disposed between these two sheets and a liquid-resistant upper sheet annularly, extending above the outer surface of the topsheet. The upper sheet is joined along its outer peripheral edge to the outer surface of the topsheet and formed substantially in its central zone with a longitudinally extending opening which is, in turn, provided along its peripheral edge with a longitudinally stretchable elastic member. With this known diaper, it is possible to prevent undesirable leakage of excretion disposed thereon from occurring along transversely opposite side edges and/or along longitudinally opposite ends of the diaper by the upper sheet which extends annularly above the outer surface of the topsheet and is joined along its peripheral edge to the topsheet.

However, the aforesaid Japanese Patent Application Disclosure No. 1993-277149 has a problem that, after urine and feces have been discharged into the opening, an amount of urine flowing on the topsheet may be mixed with loose passage, watery feces or even relatively solid feces since it is impossible for the diaper to separate feces from urine. Consequently even relatively solid feces may become watery and give the wearer an uncomfortable feeling if this watery mixture comes in contact with the wearer's skin.

SUMMARY OF THE INVENTION

It is an object of this invention to provide a disposable diaper that reliably prevents undesirable leakage of urine as well as feces discharged on the diaper from occurring along both the transversely opposite side edges and the longitudinally opposite ends of the diaper, and reliably prevents urine and feces from being mixed together.

According to this invention, there is provided a disposable diaper having absorbent body, comprising a liquid-pervious topsheet, a liquid-impervious backsheet, a liquid-absorbent core disposed therebetween. A first liquid-resistant barrier wall annularly extends above a top surface of the topsheet. The absorbent body has transversely opposite side edge portions and longitudinally opposite end portions. The barrier wall is joined along a lower peripheral edge thereof to the body so as to define a first opening substantially in a central zone of the first barrier wall. An upper peripheral edge of the first barrier wall is elastically stretchable along the first opening. The barrier wall lies in a front half section of the absorbent body that extends from a vicinity of a center line bisecting a longitudinal dimension of the absorbent body toward a front end portion of the absorbent body or in a rear half section of the absorbent body that extends from a vicinity of the center line toward a rear end portion of the absorbent body. A liquid-resistant second barrier wall annularly extending around the first barrier wall lies in the front and rear half sections of the absorbent body. The second barrier wall has a lower peripheral edge portion joined to a peripheral edge of the absorbent body so as to define a second opening substantially in a central zone of the second barrier wall and an upper peripheral edge portion thereof has an elastic stretchably along the second opening.

The disposable diaper according to this invention functions as a barrier to prevent urine and feces discharged together from being mixed together even if one of such urine and feces tends to flow. Additionally, the barrier walls annularly extend on the top surface of the topsheet and thereby prevent leakage of urine and feces discharged onto the diaper from occurring along the transversely opposite side edges as well as along the longitudinally opposite ends of the diaper.

DETAILED DESCRIPTION OF THE PREFERRED EMBODIMENT

Details of a disposable diaper according to this invention will be more fully understood from the description given hereunder with reference to the accompanying drawings.

Figure 1:
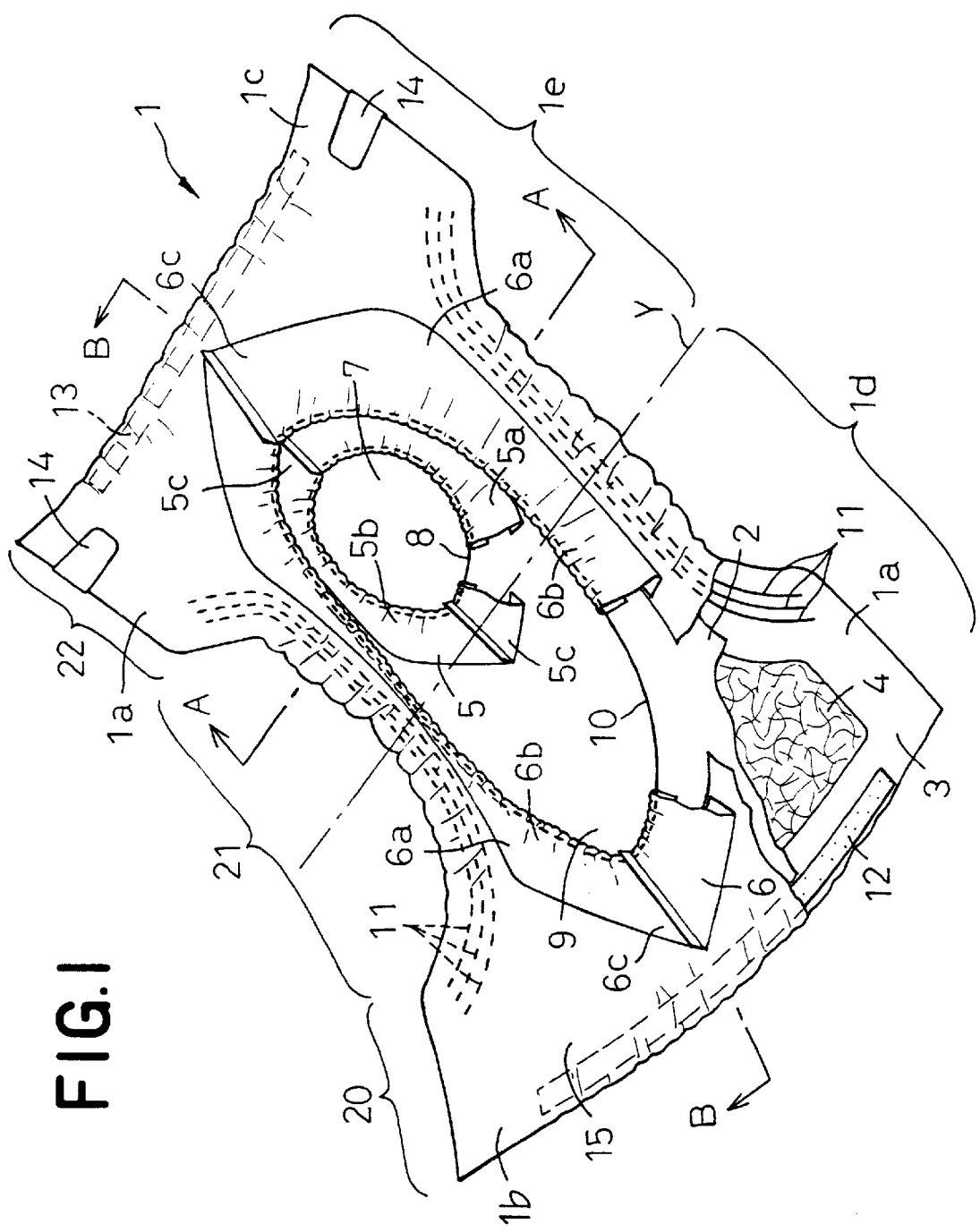
FIG. 1 is a perspective view showing a partially cutaway disposable diaper according to this invention.

FIG. 1 is a perspective view showing a partially cutaway disposable diaper according to this invention. The diaper is provided with an absorbent body 1 in the form of a laminated panel. The absorbent body 1 comprises a liquid-pervious first topsheet 2, a liquid-impervious backsheet 3, a liquid-absorbent core 4 disposed between the first topsheet 2 and the backsheet 3. A liquid-resistant inner barrier wall 5 annularly extends above the top surface of the first topsheet 2 and a liquid-resistant outer barrier wall 6 annularly extends around the inner barrier wall 5. The absorbent body 1 is longitudinally composed of a front waist region 20, a rear waist region 22 and a crotch region 21 extending between these front and rear waist regions 20, 22. The absorbent body 1 has transversely opposite side edge portions 1a, 1a longitudinally extending parallel to each other that are curved in the crotch region 21 inwardly of the absorbent body 1 so as to describe circular arcs. The absorbent body 1 also has longitudinally opposite end portions 1b, 1c transversely extending parallel to each other.

The inner barrier wall 5 lies in a rear half section 1e of the absorbent body 1 which rear half section extends from a vicinity of a center line Y bisecting a longitudinal dimension of the absorbent body 1 toward the rear end portion 1c of the absorbent body 1. The inner barrier wall 5 comprises a pair of symmetrical halves each having a lower peripheral edge portion 5a describing a circular arc, an upper peripheral edge portion 5b also describing a circular arc inside the lower peripheral edge portion 5a and longitudinally opposite ends 5c, 5c placed against and joined to the opposite ends of the other half.

In a substantially central zone of the inner barrier wall 5, a longitudinal inner opening 7 is defined in which approximately one half of the crotch region 21 and approximately one half of the rear waist region 22 are exposed. The first topsheet 2 is exposed in this first opening 7. An elastically stretchable member 8 is secured under tension to the inner barrier wall 5 along its upper peripheral edge portion 5b.

The outer barrier wall 6 lies in a front half section 1d of the absorbent body 1 which front half section extends from a vicinity of the center line Y bisecting a longitudinal dimension of the absorbent body 1 toward the front end portion 1b of the absorbent body 1 and a rear half section 1e. The outer barrier wall 6 comprises a pair of symmetrical halves each having a lower peripheral edge portion 6a describing a circular arc, an upper peripheral edge portion 6b also describing a circular arc inside the lower peripheral edge portion 6a and longitudinally opposite end portions 6c placed against and joined to longitudinally opposite end portions of the other half.

In a substantially central zone of the second outer barrier wall 6, a longitudinal outer opening 9 is defined, in which the crotch region 21 and approximately half of each of the respective front and rear waist regions 20, 22 are exposed. An upper peripheral edge portion 6b of the outer barrier wall 6 lies outside the upper peripheral edge portion 5b of the inner barrier wall 5 and the outer opening 9 surrounds the first opening 7. The outer opening 9 exposes the first topsheet 2 in the front half section 1d of the absorbent body 1 and the entire first opening 7 in the rear half section 1e of the absorbent body 1. An elastically stretchable member 10 is secured under tension to the outer barrier wall 6 along its upper peripheral edge portion 6b. A liquid-resistant second topsheet 15 extends outward beyond the lower peripheral edge portion 6a of the outer barrier wall 6.

The absorbent body 1 is provided along its side edge portions 1a, 1a with longitudinally extending elastic members 11, 11 secured under tension thereto and along its front and rear end portions 1b, 1c with transversely extending film-like elastic members 12, 13, respectively. The elastic members 12, 13 are disposed between the second topsheet 15 and the backsheet 3 and secured under tension between these two sheets 15, 3. The elastic members 11, 11 are associated with leg-openings and said elastic member 12, 13 are associated with a waist-opening. In the rear waist region 22, a pair of tape fasteners 14, 14 are attached to the side edge portions 1a, 1a of the absorbent body 1, respectively, so that these tape fasteners 14, 14 may be anchored on a rectangular strip of target tape (not shown) attached to the back surface of the backsheet 3 in the front waist region 20 of the absorbent body 1.

Referring to FIG. 1, gathers are formed along the upper peripheral edge portions 5b, 6b of the inner and outer barrier walls 5, 6, the side edge portions of the side flaps 1a, 1a as well as the end portions of the end flaps 1b, 1c of the absorbent body 1 as the elastic members 8, 10 for the inner and outer barrier walls 5, 6, the elastic members 11, 11 for the leg-opening and the elastic members 12, 13 for the waist-opening are relieved of tension.

Figure 2:
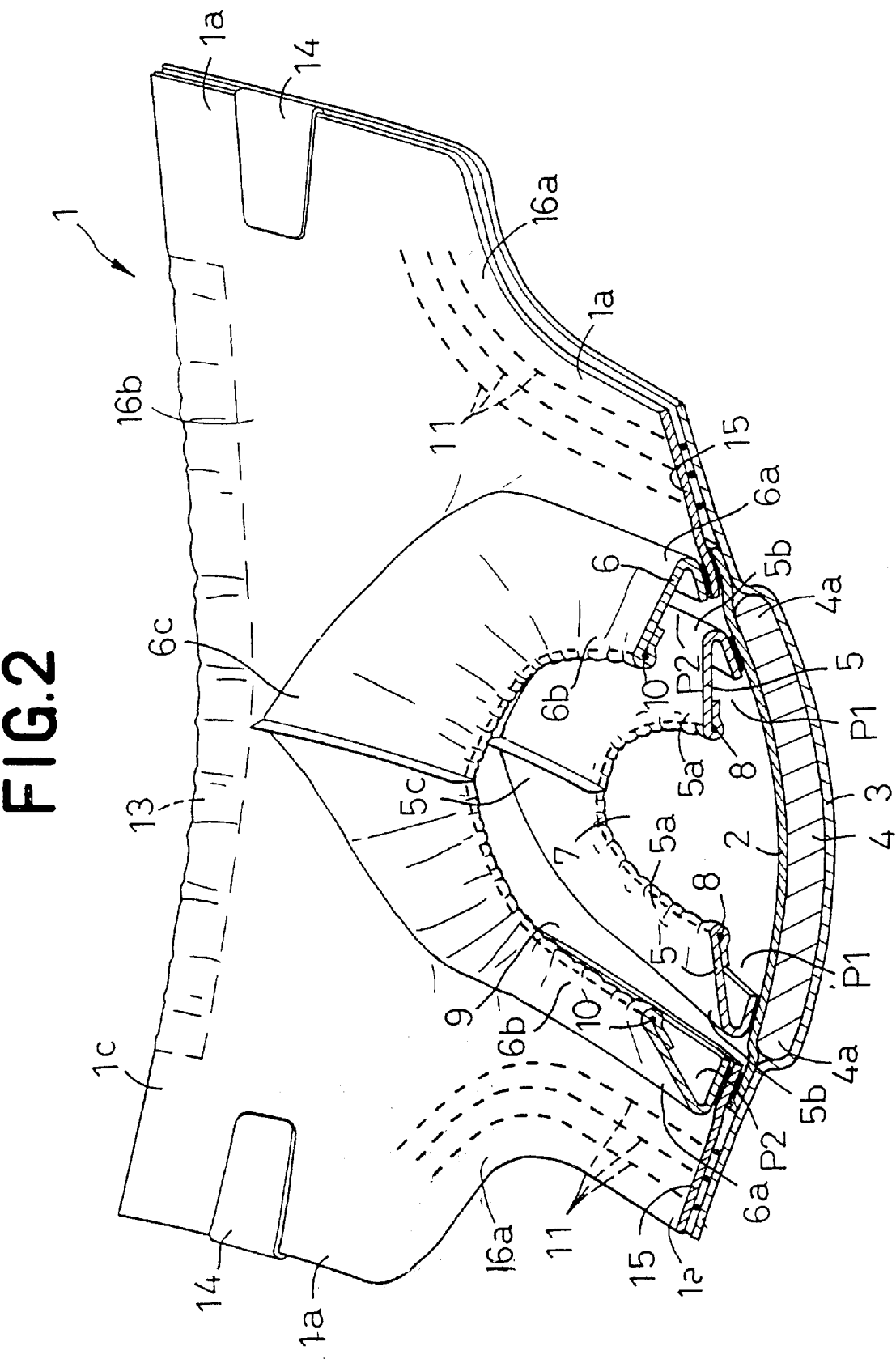
FIG. 2 is a perspective view showing the diaper partially in a sectional view taken along line A—A.
Figure 3:
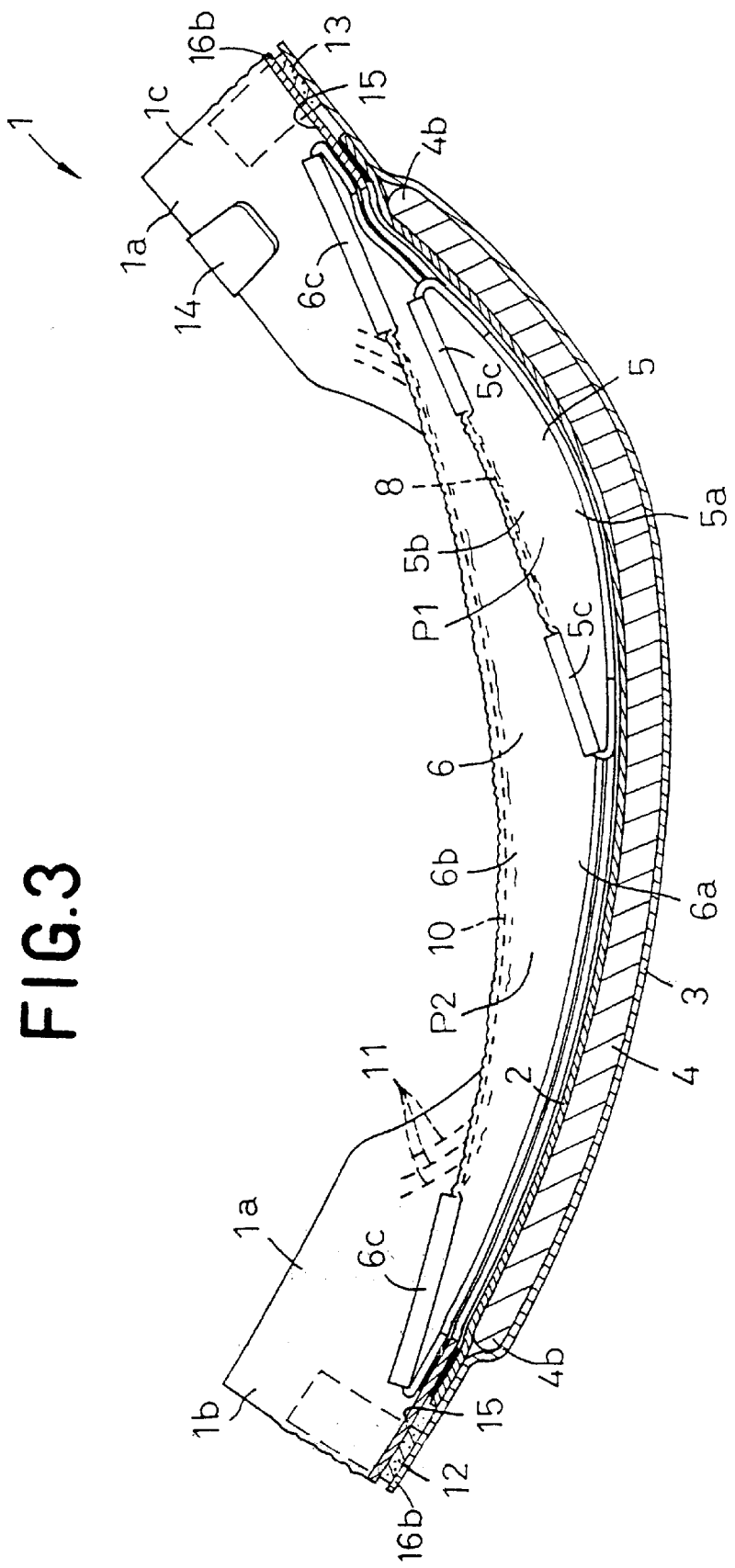
FIG. 3 is a sectional view taken along line B—B in FIG. 1.

FIG. 2 is a perspective view showing the diaper partially in a sectional view taken along line A—A in FIG. 1, and FIG. 3 is a sectional view taken along line B—B in FIG. 1. The lower peripheral edge portion 5a of the inner barrier wall 5 is partially folded inwardly of the absorbent body 1 and fixed to the top surface of the first topsheet 2. The upper peripheral edge portion 5b of the inner barrier wall 5 is also partially folded inwardly of the absorbent body 1 to cover the elastic member 8. The longitudinally opposite ends 5c, 5c of the inner barrier wall 5 are placed against and joined to each other along a line extending outward longitudinally of the absorbent body 1.

The lower peripheral edge portion 6a of the outer barrier wall 6 is partially folded inwardly of the absorbent body 1 and fixed to a top surface of the second topsheet 15 and the upper peripheral edge portion 6b of the outer barrier wall 6 is partially folded inwardly of the absorbent body 1 so as to cover the elastic member 10. The longitudinally opposite ends 6c, 6c are placed against and joined to each other along a line extending outward longitudinally of the absorbent body 1.

In the rear half of the absorbent body 1, the lower peripheral edge portion 5a of the inner barrier wall 5 is normally spaced from the lower peripheral edge portion 6a of the outer barrier wall 6 so that the first topsheet 2 may be exposed between the lower peripheral edge portions 5a, 6a of the barrier wall 5, 6. The inner barrier wall 5 cooperates with the first topsheet 2 to form a pocket P1 adapted to be opened inwardly of the absorbent body 1 and the outer barrier wall 6 cooperates with the first topsheet 2 to form a pocket P2 also adapted to be opened inwardly of the absorbent body 1 as the absorbent body 1 is curved longitudinally and transversely thereof with its inner surface inside.

The first topsheet 2 extends transversely outward slightly beyond transversely opposite side edges 4a, 4a and also extends longitudinally outward slightly beyond longitudinally opposite ends 4b, 4b of the core 4. The backsheet 3 and the second topsheet 15 extend outward transversely as well as longitudinally beyond peripheral edges of the first topsheet 2 to form side flaps 16a having the side edge portions 1a and to form end flaps 16b having the end edges 1b. The second topsheet 15 is joined to the top surface of the first topsheet 2, and to inner surface of the backsheet 3. The elastic members 11, 11 of the respective leg-openings are disposed between the backsheet 3 and the second topsheet 15 and secured under tension between these two sheets 3, 15. The core 4 is fixed between the first topsheet 2 and the backsheet 3.

The absorbent body 1 forms the pair of leg-openings and the waist-opening (not shown) when the tape fasteners 14, 14 are anchored to the strip of target tape by means of pressure-sensitive adhesive applied on the inner surface of free end portions of the respective tape fasteners 14, 14.

Urine discharged into the outer opening 9 lying in the front half section 1d of the absorbent body 1 is absorbed by the core 4 through the first topsheet 2 and feces discharged into the inner opening 7 lying in the rear half section 1e of the absorbent body 1 is also absorbed by the core 4 through the first topsheet 2. The inner barrier wall 5 functions to separate a urine absorbing zone substantially defined in the front half section Id of the absorbent body 1 from a feces absorbing zone substantially defined in the rear half section 1e of the absorbent body 1. In other words, the inner barrier wall 5 serves as a barrier to prevent feces discharged into the inner opening 7 from moving into the front half section 1d of the absorbent body 1 and/or urine discharged into the outer opening 9 from flowing into the inner opening 7. In this way, urine and feces are not mixed together.

The pocket P1 adapted to receive feces discharged onto the absorbent body 1 prevents feces from moving into the front half section 1d of the absorbent body 1 even when a relatively large amount of feces is discharged onto the absorbent body 1. Assuming that urine discharged onto the front half section 1d of the absorbent body 1 flows toward the rear end portion 1c of the absorbent body 1, such flow of urine can be guided, in the rear half section 1e of the absorbent body 1, between the lower peripheral edge 5a of the inner barrier wall 5 and the lower peripheral edge 6a of the outer barrier wall 6. Thus the absorbent body 1 enables its rear half section 1e also to absorb a flow of urine.

The first topsheet 2 may be formed from a liquid-pervious sheet such as a non-woven fabric or a porous plastic film, and preferably from a liquid-pervious and hydrophilic sheet. The backsheet 3 may be formed from a liquid-impervious plastic film or a laminated sheet consisting of a liquid-impervious plastic film and a hydrophobic nonwoven fabric, and preferably from a breathable but liquid-impervious sheet. The inner and outer barrier walls 5, 6 and the second topsheet 15 may be formed from a breathable nonwoven fabric, and preferably from a breathable but liquid-impervious nonwoven fabric. Preferably, the inner barrier wall 5 has a water pressure resistance higher than that of the outer barrier wall 6, more specifically, the inner barrier wall 5 has a water pressure resistance of 150–500 mm and the outer barrier wall 6 has a water pressure resistance of 50–300 mm. Generally, feces contains plenty of organic substances such as proteins and lipids and therefore presents a surface tension with respect to the barrier walls 5, 6 that is lower than that presented by urine. In addition to this aspect, it should be taken account that the organic substances contained in feces have an affinity for polyolefine resin. If the nonwoven fabric used as the stock material for the barrier walls is made of polyolefine resin, feces can permeate this nonwoven fabric more easier than urine. In view of this, the water pressure resistance of the inner barrier wall 5 is adjusted to be higher than that of the outer barrier wall 6 to alleviate a possibility that feces might permeate the nonwoven fabric.

The nonwoven fabric may be selected from a group including a spun lace nonwoven fabric, a needle punch nonwoven fabric, a melt blown nonwoven fabric, a thermal bond nonwoven fabric, a spun bond nonwoven fabric and a chemical bond nonwoven fabric. The component fiber for the nonwoven fabric may be selected from a group including polyolefine, polyester and polyamide fibers and polyethylene/polypropyrene or polyester conjugated fibers.

The core 4 comprises a mixture of fluff pulp and highly absorptive polymer particles compressed to a desired thickness and entirely covered with a water-pervious sheet such as tissue paper. The elastic members 8, 10, 11, 12, 13, may be formed from an elastomer such as synthetic or natural rubber or such an elastomer which has been previously secured under tension to a nonwoven fabric. Steps of fixing the core 4, attaching the elastic members 8, 10, 11, 12, 13 and joining of the elements 2, 3, 5, 6, 15 may be carried out using adhesive such as hot melt adhesive or pressure-sensitive adhesive, or a heat-sealing technique.

Alternatively, it is also possible to provide the inner barrier wall 5 in the front half section 1d of the absorbent body 1 so that the first opening 7 may be defined in this front half section 1d of the absorbent body 1. In this case, urine discharged into the inner opening 7 lying in the front half section 1d of the absorbent body 1 is absorbed by the core 4 through the first topsheet 2 and feces discharged into the outer opening 9 lying in the rear half section 1e of the absorbent body 1 is also absorbed by the core 4 through the first topsheet 2. In the front half section 1d, the inner barrier wall 5 serves as a barrier to prevent feces from moving into the inner opening 7 and/or urine from flowing into the rear half section 1e of the absorbent body 1. In this way, possible mixing of urine and feces together can be avoided.

This invention is applicable not only to the open-type diaper as shown but also to pants-type diapers.

What is claimed is:

1. A disposable diaper having an absorbent body, comprising:
   a liquid-pervious topsheet;
   a liquid-impervious backsheet;
   a liquid-absorbent core disposed between the liquid-pervious topsheet and the liquid-impervious backsheet; and
   a first liquid resistance barrier wall annularly extending above a top surface of said topsheet,
   the absorbent body having transversely opposite side edge portions and longitudinally opposed end portions,
   said first liquid-resistant barrier wall being joined along a lower peripheral edge thereof to the remainder of said absorbent body so as to define a first opening substantially in a central zone of said first liquid-resistant barrier wall, and an upper peripheral edge of said first liquid-resistant barrier wall being elastically stretchable along said first opening,
   said first liquid-resistant barrier wall lying in one of a front half section of said absorbent body extending from the vicinity of a center line bisecting a longitudinal dimension of said absorbent body toward a front one of said end portions of said absorbent body or of a rear half section of the absorbent body extending from the vicinity of said center line toward a rear one of said end portions of said absorbent body;
   said disposable diaper further comprising a second liquid-resistant barrier wall annularly extending around said first liquid-resistant barrier wall and lying in said front and rear half sections of said absorbent body,
   said second liquid-resistant barrier wall having a lower peripheral edge portion joined to a peripheral edge of said absorbent body so as to define a second opening substantially in a central zone of said second liquid-resistant barrier wall and an upper peripheral edge portion thereof with elastic strechability along said second opening.

2. A disposable diaper according to claim 1, wherein the first and second fluid-resistant barrier walls each have lower peripheral edges and the lower peripheral edge of said first liquid-resistant barrier wall lies at a distance inwardly of an outer edge of said absorbent body greater than the lower peripheral edge of said second liquid-resistant barrier wall lies so that the liquid-previous topsheet is exposed between the lower peripheral edges of said first and second liquid-resistant barrier walls.

3. A disposable diaper according to claim 1, wherein the first and second liquid-resistant barrier walls have upper peripheral edges and the upper peripheral edge of said first liquid-resistant barrier wall lies at a distance inwardly of an outer edge of said absorbent body greater than the upper peripheral edge of said second liquid-resistant barrier wall so that an entire area of said first opening is exposed in said second opening.

4. A disposable diaper according to claim 1 wherein said first liquid resistant barrier wall lies in the front half section of said absorbent body and said first and second liquid-resistant barrier walls are formed from a nonwoven fabric and said first liquid-resistant barrier has a water pressure resistance that is higher than a water pressure resistant of said second liquid-resistant barrier wall.

* * * * *